United States Patent [19]
Buntzen et al.

[11] Patent Number: 5,081,900
[45] Date of Patent: Jan. 21, 1992

[54] RESONANCE DAMAGE PROCESS

[76] Inventors: Rodney R. Buntzen, 9380 Lemon Ave., La Mesa, Calif. 92041; Robert R. Hammond, 535 Savoy, San Diego, Calif. 92106

[21] Appl. No.: 337,030

[22] Filed: Feb. 23, 1973

[51] Int. Cl.⁵ .......................... B64D 1/04; F41F 5/00; G01K 10/00
[52] U.S. Cl. .................................. 89/1.11; 102/201; 181/0.5; 181/142; 381/156
[58] Field of Search ....... 181/0.5 AG, 0.5 R, 0.5 NP, 181/0.5, 142; 250/83.3 H, 83.3 UV; 331/94.5 A; 73/67.2 P, 67.3; 89/1.11; 381/15 B

[56] References Cited
U.S. PATENT DOCUMENTS

| | | | |
|---|---|---|---|
| 3,322,231 | 5/1967 | Gournay | 181/0.5 AG |
| 3,392,527 | 7/1968 | Gilmour et al. | 331/94.5 A |
| 3,489,645 | 1/1970 | Daiber et al. | 331/94.5 A |
| 3,532,181 | 10/1970 | DeMaria et al. | 181/0.5 R |
| 3,723,703 | 3/1973 | Ehlers et al. | 331/94.5 A |

OTHER PUBLICATIONS

12/14/49, General Electric News Bureau, Pneumatic Strip Tester, pp. 29-30.
Halliday et al, Physics, 64, pp. 372-375, "Forced Oscillations and Resonance".
White, "Elastic Wave Generation by . . . Electromagnetic Wave Absorption", '63, pp. 2123-2124, Journal of Appl. Phys. vol. 34.
White, "Generation of Elastic Waves by Transient Surface Heating", 12/63, pp. 3559-3567, Journal of Appl. Phys. vol. 34, #12.
DeMaria et al, "Picosecond Laser Pulses", 1/69, pp. 2-25, Proceedings of IEEE, vol. 57, #1.

*Primary Examiner*—Nelson Moskowitz
*Attorney, Agent, or Firm*—Harvey Fendelman; Thomas Glenn Keough

[57] ABSTRACT

A method and system for the production of stress waves in a solid target employs a pulsed source of coherent photon energy. the pulse repetition frequency of the photon energy is chosen in dependence upon the physical dimension and nature of the selected material so as to reinforce reflected compression and rarefaction waves within the material.

4 Claims, 2 Drawing Sheets

RESONANCE DAMAGE PROCESS

STATEMENT OF GOVERNMENT INTEREST

The invention described herein may be manufactured and used by or for the Government of the United States of America for governmental purposes without the payment of any royalties thereon or therefor.

FIELD OF THE INVENTION

This invention pertains to the field of electro-optics and hydrodynamics. More particularly, this invention pertains to inneraction of photon energy with solid bodies. In still greater particularity, the invention pertains to the generation of compressional or stress waves within a body of solid material by means of photon inneraction therewith. In still greater particularity, but without limitation thereto, this invention pertains to the generation of shock waves within a solid body of means of a pulsed laser beam.

DESCRIPTION OF THE PRIOR ART

Generally speaking, present methods of generating high stresses within a solid material depend upon the rapid input of a sufficient amount of energy within a very short time duration, i.e. a single pulse. For example, high stresses and spallation of solid materials from the back surface of a solid body have been produced by a single high-power pulse of electromagnetic energy. Of course, direct input of mechanical energy is also well known.

Likewise, past uses of radiant energy to produce high levels of mechanical stress have depended upon a single application of a high intensity radiation. In order to get sufficiently high energy over a relatively small area of the solid material, early applications devised large focusing and light control systems. However, as in the case of mechanical energy and electromagnetic energy, these early devices, termed solar furnaces, employed but a single application of the radiant energy.

With the advent of lasers, it has become possible to concentrate a sufficiently high amount of radiant or photon energy in a very small area upon the surface of a solid material and thereby generate within the material a mechanical shock wave. This shock wave is produced as a reaction to the energy from the laser interacting with a very thin region of the material immediately adjacent the surface. That is, a small portion of the surface of the material is vaporized under the intense radiation afforded by the laser and, in response to this destructive thermal reaction, a shock wave is generated within the material.

As with the other forms of shock wave generated by prior art systems, the shock wave travels through the material in a well understood manner in dependence upon the nature of the material, its physical dimensions, and its particular shape. When the energy encounters a change of propagation medium as might be experienced by impinging another boundary of the solid material, a portion of the shock wave is reflected back toward the origin. As the repeated traversals of the material take place, the amplitude of the shock wave and its propagation path are altered in the well understood manner. This alteration depends upon the material and shape of the object.

The recognized advantages of using lasers to generate such mechanical shock waves in the prior art have been limited to their ability to apply a large amount of energy over a very small area on the particular material and to do so in precisely controllable periods of extremely short duration. Obtaining very high mechanical stress waves has, in the past, required laser sources having very high power outputs.

As a consequence of the high power, the laser heats up and requires relatively long duty cycles. Additionally, the large single pulse techniques of the prior art are severely limited in propagation by atmosphere interaction with the radiant energy beam. This interaction with the beam expends the energy thereof to leave the intended target little affected by the radiant energy reaching it through a propagation path in the atmosphere. There are many applications where such limitations of prior art laser stress generating systems have prohibited their use.

SUMMARY OF THE INVENTION

This invention uses a relatively high energy laser beam which is modulated or pulsed at a high frequency which corresponds to the traverse time of the mechanical energy within the irradiated material. This pulse rate is chosen such as to reinforce the shock wave which is returned to the irradiated surface as a reflected rarefaction wave such as to produce a mechanical shock wave within the irradiated material which increases in value, pulse-by-pulse, until the desired level of mechanical stress has been obtained. The particular level of mechanical stress or pressure is, of course, dependent upon the intended purpose of the pressure generation. For example, in some thermonuclear reactions, it is desirable to generate a sufficient pressure within a body of fusionable material to initiate neutron or other nuclear emissions therein. Of course, in some applications, for example, stress testing, it may be desired to induce an internal mechanical stress within the radiated material to cause its mechanical failure.

STATEMENT OF THE OBJECTS OF INVENTION

It is accordingly an object of this invention to provide an improved method and system for the generation of high compression mechanical stresses.

It is further an object of this invention to provide a method and system for producing mechanical stresses in a solid material by means of photon energy.

It is another object of the present invention to produce mechanical stresses within a body of solid material by the use of a modulated source of coherent photon energy.

A further object of the present invention is to provide for the generation of compressional waves within a solid body by means of a pulsed laser beam.

It is a further object of the present invention to provide a method and system for the generation of shock waves in a body of solid material by irradiating the material with a source of photon energy which is modulated as a function of the dimensions and physical properties of the solid body.

Another object of the present invention is to provide a method and apparatus for the generation of zones of compressional energy in a solid body in response to the application of pulsed radiant energy at a plurality of points on the surface of the solid body.

These and other objects of the invention will become more readily apparent from the ensuing specification when taken with the drawings.

DESCRIPTION OF THE PREFERRED EMBODIMENT

Figure 1:
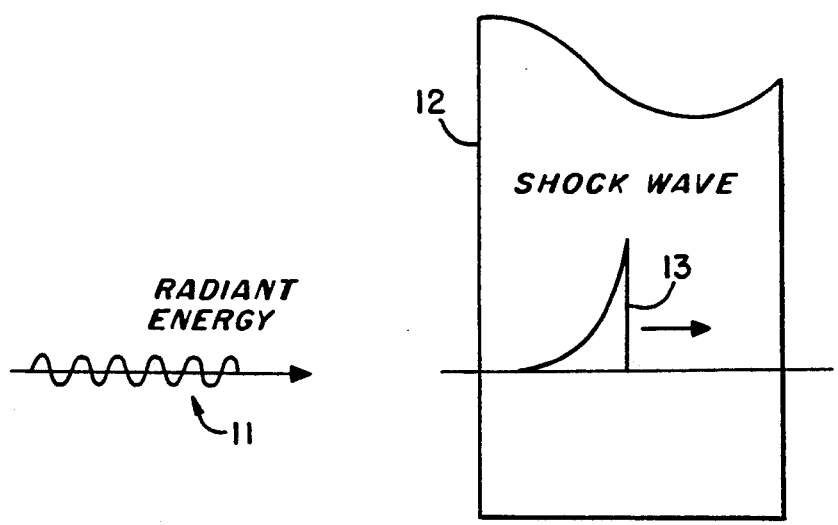
FIG. 1 is a schematic illustration showing the generation of a shock wave in response to a pulse of radiant energy.

Before referring to FIG. 1, a discussion of the mode of operation of the invention will be useful. The modern development of sources of coherent photon energy, e.g. lasers, capable of operation at relatively high instantaneous power levels has given rise to considerable interest in the interaction of the radiant energy output of such sources with solid materials. For example, it was early recognized that a plate of solid material could have high level stress forces or shock wave generated as a result of a single high power concentration of radiant energy. The generation of power levels of radiant energy sufficient to accomplish the generation of stresses within the solid material required extremely high-powered laser sources which are characterized as having a rather limited duty cycle.

When a radiation pulse impinges on a metallic surface, the non-reflected portion of the incident energy is absorbed as heat in a thin layer near the surface and is simultaneously transported deeper into the target by conduction. Thus, aside from the momentum of the reflected photons themselves (which is entirely negligible for our purposes), no net momentum transfer occurs. If, however, the pulse is sufficiently intense, the heat content in the surface layer may instantaneously become high enough to cause a "boil-off" of metallic particles before conduction can carry the heat away. The amount of material vaporized is generally very small, but, since the total momentum in the system is conserved, the remaining irradiated material experiences an impulse away from the laser projector, which balances the momentum of the expanding metallic gas on the irradiated side. Thus, the "momentum transfer" phenomenon is poorly named, since no momentum is, in principle, transferred.

Since the amount of material vaporized is generally extremely minute compared to the over-all mass of the irradiated material, however, it is convenient and appropriate to neglect the mass change altogether and to interpret the momentum delivered to the material as due to a true impulse applied to the exposed surface. Indeed, for practical calculations, some such procedure would appear to be necessary. To explicitly follow the motion of the gas would require a computational space grid of prohibitively fine resolution, since the amount of material vaporized is typically many orders of magnitude smaller than the thickness of the particular irradiated material under consideration. Furthermore, an extremely elaborate equation of state would be required to describe the true phenomena involved in this situation.

Considering the case of the high-energy laser pulse applied to one face of a body of metallic material, the heating of the irradiated surface will generate a mechanical shock wave which will be propagated through the plate and eventually reach the opposite side. This positive pressure shock will then be reflected as a negative pressure rare-faction, or tension wave, which will retraverse the target to impinge the irradiated surface. Likewise, the negative pressure wave will again be reflected as a shock wave.

These stress waves are both dissapitive and dispersive. As a result of the dissapative and dispersive nature of the waves the strength of each successive wave traversal will decrease, or be damped, with time. As a result, if the desired level of mechanical stress is not obtained in the first traversal of the pulse it will, naturally, not be obtained in subsequent stress wave traversals. However, it has been discovered that if the input power to the laser where modulated in a periodic fashion with respect to time, mechanical shock waves and forces might be generated within the radiated material due to time-dependent dynamic stresses induced by the modulated laser beam.

There are many instances where generation of a mechanical shock wave of a predetermined intensity is desired to be generated within a radiated material. In the simplest case, it may be desired to simply cause mechanical failure, sometimes termed "spalling". However, there are other uses for internal pressures generated within a solid material which will be familiar to those versed in the various metalurgical arts, metal bonding arts, crystallographic arts, and the solid state physics arts. As an example, it is sometimes desired to create a zone of high pressure within a quantity of fissionable material in order to trigger a thermonuclear reaction therein.

As will be recognized by those familiar with the field of mechanical dynamics, the response of the subject matter to the pulses of irradiated energy depends on a number of parameters. Some of the more obvious of these are:

1. The composition of irradiated material,
2. The thickness of the irradiated material,
3. The energy delivered per radiation pulse,
4. The area of the material covered by the photon energy,
5. The time duration of the radiation pulse,
6. The repeitition rate of the pulses of radiant energy, and
7. The wave length of the incident radiation.

Clearly then, a study involving variations of each of these parameters would be an extremely lengthy discussion. Such a discussion is not required for the understanding of the invention and if such a complete description is desired, standard works in the field of solid state physics provide detailed discussions of these various phenomena and how they interact.

By assuming that some of the variables remain constant, such as, for example, the flux density over the irradiated area, the wave length of the radiating energy, the energy delivered per pulse, the time duration of the individual pulses, and the repetition frequency, a reasonably good approximation of the one dimensional phenomena may be obtained.

Referring now to FIG. 1, the pulse of eradiated energy 11 is shown approaching a target 12. A previous pulse of radiant energy similar to that illustrated at 11 has generated within target 12, a shock wave 13 which traverses the target in the direction indicated by the arrow.

Figure 2:
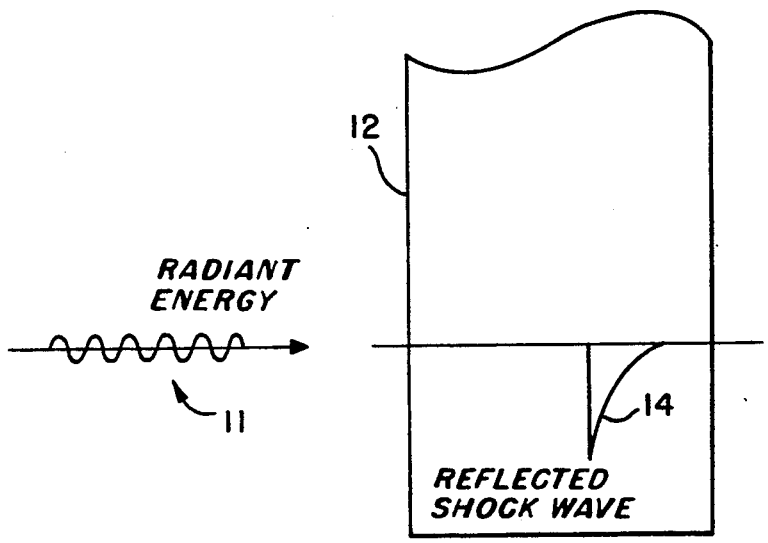
FIG. 2 is a schematic illustration showing the reflection of the shock wave producing rarefaction wave caused by the shock wave shown in FIG. 1.

Referring to FIG. 2, the condition of target 12 is shown at a finite time later than shown in FIG. 1, as indicated by the closer proximity of radiant energy pulse 11. As shown, shock wave 13 has been reflected from the non-irradiated face of solid material 11 as a negative or tension wave to retraverse the path of shock wave 13 to irradiated face of material 12.

Figure 3:
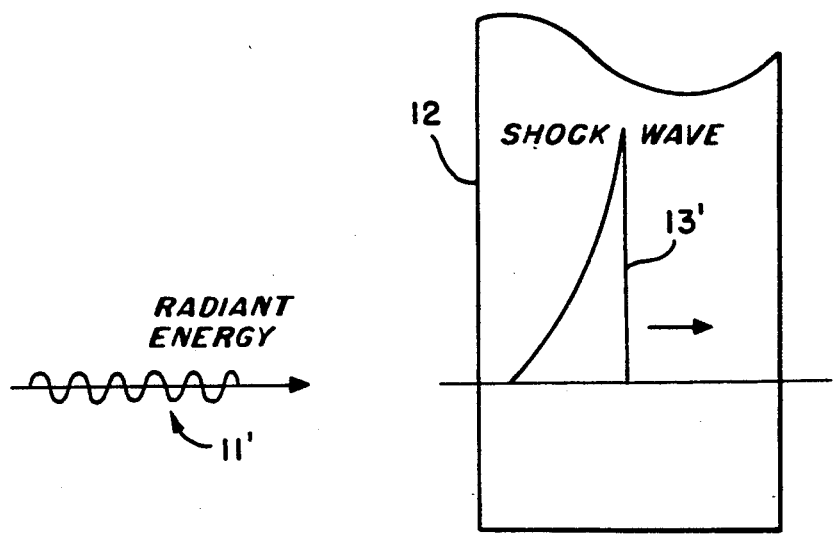
FIG. 3 illustrates the reinforcement of the shock wave by a subsequent pulse of radiant energy.

Referring to FIG. 3, the shock wave 14 has impinged irradiated face of the material 12 and been reinforced by radiant energy pulse 11 to produce a shock wave 13' having a magnitude greater than that produced by radiant energy pulse 11. As shown, another pulse of radiant energy 11' is approaching subject material 12.

Thus, it may be seen that the successive pulses of radiant energy may be timed to produce a shock wave in material 12 having a magnitude considerably greater than that possible by a single pulse of the radiant energy. Thus, it may be seen that the composite effect of the plurality of pulses of radiant energy may be the generation within material 12, a shock wave having the desired mechanical properties.

Figure 4:
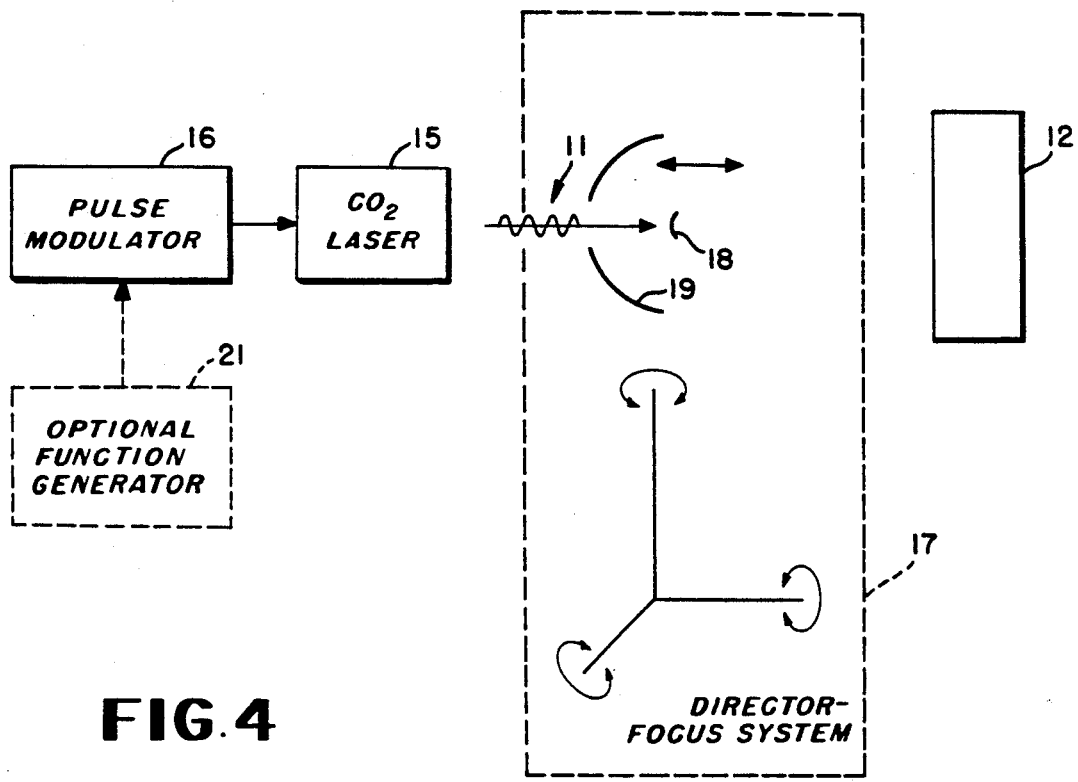
FIG. 4 is a block diagram of the system of the invention.

Referring to FIG. 4, it may be seen that the burst of radiant energy 11 is emitted from a laser 15 in response to a modulation pulse provided by a conventional pulse modulator 16. Burst of radiant energy 11 is focused and directed to material 12 by means of a director focus system 17.

The particular optics of director-focus system 17, of course, depend upon the particular wave length of the radiant energy pulse 11. That is, director-focus system 17 should be of a high efficiency. Assuming that laser 15 is a carbon dioxide laser, as illustrated, the optics of director focus system 17 may be polished metallic copper. In the illustrated embodiment, a Cassegrainian system is employed comprising a primary reflector 18 and a secondary reflector 19. Focus is obtained by moving reflectors 18 and 19 with respect to one another in a direction indicated by the double-headed arrow.

The entire director focus assembly 17 may be mounted to rotate in the three coordinates, as indicated, so as to direct radiant energy pulses 11 to the solid material 12 in a variety of spaced locations.

If the precise dimensions of the solid material 12 are known, pulse modulator 16 may be set to provide a reinforcement of the shock waves in a simple mode described in connection with FIGS. 1 through 3. In practical applications, it has been observed that a plurality of frequencies provide reinforced resonances for a single specimen of solid material. For example, when the irradiated material was a piece of aluminum one millimeter thick, one resonance peak occurred at 345 nanosecond pulse spacing corresponding to the primary transit time illustrated in FIGS. 1 through 3. However, additional resonances were noted at appoximately 30 nanosecond intervals, i.e. second peak occurring at 375 nanoseconds etc. The reason for the occurrence of the secondary resonant peaks is less obvious than that for the primary resonant peak. However, it is hypothized that they are due to a plastic non-linear behavior of the material under the high stress levels generated. Under these stress levels, the sharp leading edge of the pulse illustrated in FIGS. 1 through 3 degenerates into a series of crests having somewhat lower amplitude on each successive crest.

If the frequency of modulator 16 was adjusted slightly such that the second pulse of radiant energy 11' coincided with the second or third of these smaller minor crests, it may be easily understood that resonance and reinforcement would occur at this frequency. As a result of this phenomena, it has been possible to produce reinforcing resonant pulses by modulating laser 15 with bursts of very short pulses at approximately 5 nanosecond intervals. Such a modulation arrangement results in reinforcement resonances in a wide variety of target materials, shapes, sizes and orientations with respect to laser 15.

In some applications, where exact dimensions of the radiated material 12 are unknown, it may be desirable to sweep pulse modulator 16 through a range of modulation frequencies. Such a sweeping may be accomplished by the use of a conventional ramp generator such as shown at 21. Of course, modulator 16 may be programmed by other functions than linear ramps such as, for example, an up-slide and down-slide generator or a plurality of discrete frequencies sequentially applied to modulator 16.

Figure 5:
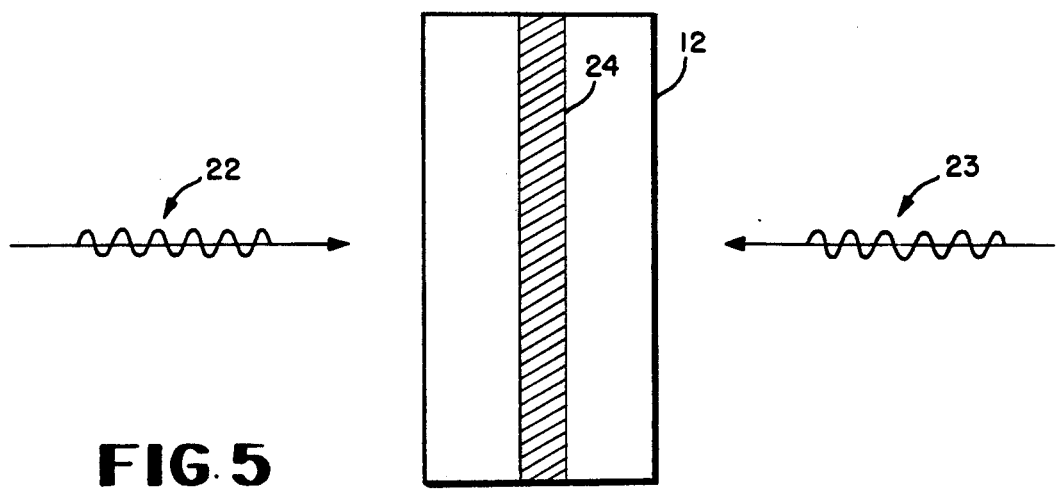
FIG. 5 illustrates how a plurality of the systems used in FIG. 4 may be used with a single solid body.

Referring to FIG. 5, an arrangement is shown where irradiated material 12 may be irradiated by photon energy arriving simultaneously from each side. Such a burst of energy is illustrated at 22 and 23. As would be expected, this arrangement may produce a zone, illustrated at 24, within irradiated solid material 12 where the shock waves from each pulse of radiant energy 22 and 23 reinforce one another to produce a zone of high pressure.

This arrangement may be affected by using a beam splitter in the director-focus system 17, or, alternatively, a second source of coherent photon energy modulated by pulse modulator 16 may be placed on the opposite side of solid material 12.

MODE OF OPERATION

Although the foregoing description is sufficient to enable one to construct the system of the invention, the invention and its method of practice will be better understood with reference to the following preferred mode of operation. As previously suggested, the invention may be illustrated in its practice by irradiating a speciment of aluminum 12 having a thickness of approximately one millimeter by radiant energy emission from a carbon dioxide gas laser 15. The $CO_2$ laser has a wave length output of approximately 10.6 microns and is pulsed to produce 10 nanosecond pulse duration pulses and focused by means of metallic copper director focus system 17 to produce irradiating energy of approximately two joules/cm$^2$.

Energy concentrations of each pulse depend upon the pulse length as determined by modulator 16. Modulator 16 is a conventional pulse generating trigger mechanism and it may be adjusted to produce such pulses at 5 nanosecond intervals. In this configuration, destructive pressures are quickly generated within the specimen. When the pulse interval is adjusted to cause reverberation with the reflected wave as determined by the transit time of a shock wave in the specimen, pressures may be generated to the same level as in the shorter interval thereby confirming the reinforcement or resonance operational mode. With a specimen having a thickness of 1 millimeter and made of aluminum this interval corresponds to twice the plate thickness (i.e. two millimeters) divided by the ambient speed of sound in aluminum ($5.35 \times 10^5$ cm/sec) or 374 nanoseconds.

By employment of suitable optics within director-focus system 17, other types of lasers may be accommodated in the practice of the invention and, likewise, other modulation frequencies may be provided by pulse modulator 16 to accomodate other targets. When the precise physical dimensions and properties of the target are unknown, the optinal functional generator 21 may be operated to sweep pulse modulator 16 over a spectrum of modulation frequencies so as to include an interval of pulse rates corresponding to the dimensions and natures of the expected range of target materials.

If it is desired to generate a zone of high pressure at an interior region of a particular specimen, the laser energy may be directed symetrically to the solid material so as to impinge opposite sides thereof and, thereby, generate a reinforced zone of high pressure in the interior of the irradiated material. As previously noted, this may be accomplished by either the use of plural laser generators or, alternatively, a director-focus system 17 providing for plural beam outputs.

The foregoing description taken together with the appended claims constitute a disclosure such as to enable a person skilled in the electronic and optic arts and having the benefit of the teaching contained herein to make and use the invention. Further, the structure herein described meets the objects of invention, and generally constitute a meritorious advance in the art unobvious to such a skilled worker not having the benefit of these teachings.

What is claimed is:

1. A method of generating destructive high pressures within a body of solid material comprising the steps of:
    generating a beam of coherent photon energy;
    modulating said beam to produce a train of pulses having a pulse duration and recurrence rate that is a predetermined function of the physical properties of the body of solid material including thickness along a predetermined axis, said step of modulating including interruption of the beam to produce pulse intervals corresponding to the time of two-way transit of sound within the solid body plus a time interval corresponding to the delay afforded secondary components of the shock wave due to the plastic deformation thereof resulting from the energy transfer of previous pulses so as to reinforce said secondary pulses to a predetermined level; and
    directing said beam of modulated coherent photon energy along said predetermined axis to impinge the body of solid material to produce momentum transfer shock waves therein.

2. A method of generating destructive high pressures within a body of solid material comprising the steps of:
    generating a beam of coherent photon energy;
    modulating said beam to produce a train of pulses having a pulse duration and recurrence rate that is a predetermined function of the physical properties of the body of solid material including thickness along a predetermined axis, said step of modulating including pulsing the beam at a time varying rate to sweep the pulse interval through a predetermined range of values at a rate which will assure the effective reinforcement of photon generated shock waves over a predetermined range of target sizes; and
    directing said beam of modulated coherent photon energy along said predetermined axis to impinge the body of solid material to produce momentum transfer shock waves therein.

3. A method of generating destructive high pressures within a body of solid material comprising the steps of:
    generating a beam of coherent photon energy, said step of generating including the operation of a laser optical beam generator having an output wavelength of approximately ten and six-tenths microns;
    modulating said beam to produce a train of pulses having a pulse duration and recurrence rate that is a predetermined function of the physical properties of the body of solid material including thickness along a predetermined axis; and
    directing said beam of modulated coherent photon energy along said predetermined axis to impinge the body of solid material to produce momentum transfer shock waves therein, wherein the step of directing said beam of modulated energy causes the impinging energy to fall on two separated areas and being directed so as to cause the shock waves produced thereby to reinforce at a predetermined area within the body of solid material.

4. An apparatus for generating high pressures within a body of solid material according to claim 3 in which the modulating means includes a function generator to sweep the modulating signal through a predetermined range of pulse recurrence frequencies to accomodate a predetermined range of bodies of solid material.

* * * * *